United States Patent [19]

Tsukamoto et al.

[11] 4,434,162

[45] Feb. 28, 1984

[54] PHOSPHONIC ACID ESTER, PHARMACEUTICAL COMPOSITIONS CONTAINING THE SAME AND METHOD OF USING THE SAME

[75] Inventors: Goro Tsukamoto, Toyonaka; Toshihiko Kohno, Sakai; Koichiro Yoshino, Osaka; Tominori Morita, Nishinomiya; Keizo Ito, Osaka; Takashi Nose, Nara, all of Japan

[73] Assignee: Kanebo, Ltd., Tokyo, Japan

[21] Appl. No.: 366,415

[22] Filed: Apr. 7, 1982

Related U.S. Application Data

[63] Continuation-in-part of Ser. No. 235,124, Feb. 17, 1981, abandoned.

[51] Int. Cl.³ ............... C07D 277/66; A61K 31/425
[52] U.S. Cl. ..................... 424/200; 548/113
[58] Field of Search ............... 548/113; 424/270, 200

[56] References Cited

U.S. PATENT DOCUMENTS 4,232,010 11/1980 Tsukamoto et al. ............ 548/113

Primary Examiner—John M. Ford
Attorney, Agent, or Firm—Wenderoth, Lind & Ponack

[57] ABSTRACT

A phosphonic acid ester of the formula

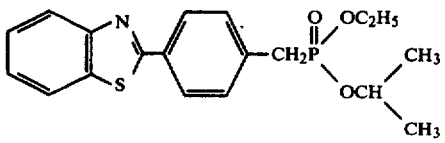

exhibits calcium-antagonistic, coronary vasodilating and hypotensive activities. Pharmaceutical compositions containing the same are useful for the prophylaxis and treatment of circulatory organ diseases such as angina pectoris, hypertension and the like.

3 Claims, No Drawings

PHOSPHONIC ACID ESTER, PHARMACEUTICAL COMPOSITIONS CONTAINING THE SAME AND METHOD OF USING THE SAME

This application is a continuation-in-part application of Ser. No. 235,124, filed Feb. 17, 1981 (now abandoned).

This invention relates to a novel phosphonic acid ester, pharmaceutical compositions containing the same and a method of using the same.

It has been well-known that various organophosphoric acid esters exhibit an acetylcholine esterase-inhibitory activity and have been used as insecticides. However, little has been known about the biological activity of organophosphonic acid esters. Japanese Laid Open Patent Application No. 3536/1978 discloses an anti-inflammatory composition containing 2-(benzothiazol-2-yl)-5-picolinylphosphonic acid diethyl ester. In U.S. Pat. No. 4,232,010 issued to Goro Tsukamoto et al., it has been reported that a phosphonic acid ester of the formula:

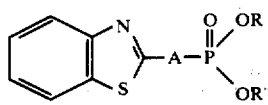

wherein A is

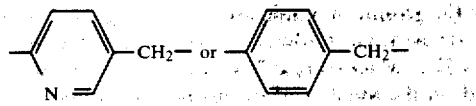

and R is a lower alkyl, exhibit a calcium-antagonistic activity.

We have now discovered that an asymmetric phosphonic acid ester of the formula

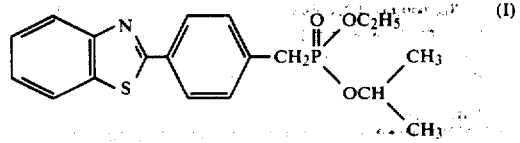 (I)

exhibits remarkable calcium-antagonistic, coronary vasodilating and hypotensive activities with less toxicities and, therefore is useful in the prophylaxis and treatment of circulatory organ diseases such as angina pectoris, hypertension, etc.

The compound of the invention is named 4-(benzothiazol-2-yl)benzylphosphonic acid isopropyl ethyl ester.

The phosphonate of the formula (I) may be synthesized by various methods.

For example, the compound (I) may be produced by reacting a compound of the formula

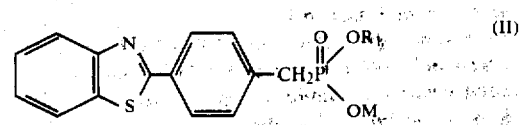 (II)

wherein $R_1$ is ethyl or isopropyl, and M is a metal atom or quaternary ammonium group, with a halide of the formula $R_2X$ wherein $R_2$ is different from $R_1$ and is ethyl or isopropyl, and X is a halogen. The starting phosphonic acid mono-ester (II) may be prepared by hydrolyzing a corresponding symmetric di-ester with an aqueous solution of a metal hydroxide and then optionally exchanging from the metal cation into ammonium cation with a tetra-alkylammonium hydrogen sulfate. Preferable examples of metal hydroxides include alkali metal hydroxides and alkaline earth metal hydroxides. Preferable examples of said tetra-alkylammonium hydrogen sulfates include tetra-isobutylammonium hydrogen sulfate.

Examples of compounds of the formula $R_2X$ include ethyl chloride, ethyl bromide, ethyl iodide, isopropyl bromide, isopropyl iodide, and the like. The reaction may be performed by heating the reactants in an aprotic polar solvent such as dimethylformamide, DMSO or diglyme at a temperature from room temperature to the boiling point of the solvent.

The compound of the formula (I) may also be produced by reacting a compound of the formula:

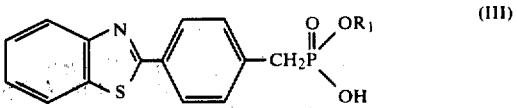 (III)

wherein $R_1$ is ethyl or isopropyl, with a diazoalkane of the formula $N_2=R_3$ wherein $R_3$ is $>CHCH_3$ or $>C(CH_3)_2$. The starting compound (III) may be prepared by hydrolyzing a corresponding symmetric phosphonic acid dialkyl ester with a metal hydroxide and then treating with an acid. An excess of said diazoalkane is reacted with said compound (III) in a solvent such as alkanols, tetrahydrofuran, dioxane, or diethyl ether at a temperature from $-10°$ C. to the boiling point of the solvent. The desired compound may be easily obtained in a high yield by simply evaporating the reaction mixture and recrystallizing the residue.

The compound of the formula (I) may generally be produced by reacting a compound of the formula:

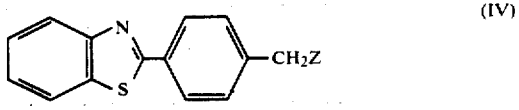 (IV)

wherein Z is a halogen atom or tosyl group with dialkyl phosphite of the formula:

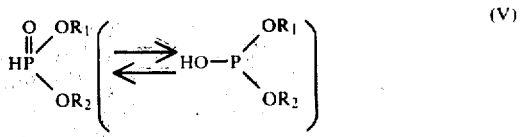 (V)

wherein $R_1$ and $R_2$ are different and are ethyl or isopropyl, in an inert solvent in the presence of a base. The reaction may be carried out at a temperature from room temperature to the boiling point of the solvent. Usable examples of the base include metallic sodium, metallic potassium, sodium hydride, sodium amide and the like. Examples of inert solvent include benzene, tetrahydrofuran, dimethylformamide, dimethylsulfoxide and the like.

Alternatively, the above compound of the formula (IV) may be reacted with a trialkyl phosphite of the formula:

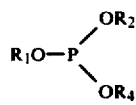

(VI)

wherein $R_1$ and $R_2$ are as defined above, and $R_4$ is a lower alkly, whose carbon number is not larger than 2, in the presence or absence of an inert solvent such as ester or diglyme at a temperature from room temperature to 200° C., preferably from 100° C. to 150° C. Examples of said trialkyl phosphite of the formula (VI) is diethyl isopropyl phosphite.

The effectiveness of said phosphonate will now be shown by way of test in laboratory animals.

1. Action on Coronary Blood Flow (a) Action on the isolated guinea pig heart.

Male guinea-pigs with body weights from 400 to 500 g were slaughtered and promptly thoractomized. After the ascending aorta was cannulated, the heart was enucleated. By the method of Langendorff, this isolated heart was perfused with the Krebs-Henseleit fluid oxygenated with a gaseous mixture of 95% $O_2$ and 5% $CO_2$ at the fluid temperature of 34±1° C. and the perfusion pressure of 60 cm $H_2O$, and the test compound was infused. The coronary flows before and after infusion were measured and the percent gain in coronary flow was obtained. The coronary flow was measured with a square-wave electromagnetic flowmeter (Nihon Kohden, MF-26) with an extracorporeal probe (Nihon Kohden, FE) set at the top of the cannula and recorded with a multipurpose polygraph (Nihon Kohden, RM-85). The test compound was dissolved in propylene glycol to a concentration of 100 γ/ml and 0.1 ml of the solution was infused at the rate of 0.1 ml/min. The results are shown in Table 1. For reference, the corresponding data on diltiazem is also shown.

TABLE 1

| Compound | No. of cases | Increase in coronary flow (Δ% ± standard error) |
|---|---|---|
| 4-(Benzothiazol-2-yl)benzyl-phosphonic acid ethyl isopropyl ester | 7 | 76.9 ± 24.4 |
| Diltiazem | 13 | 66.0 ± 7.1 |

(b) Intravenous administration into dogs.

Increase in coronary blood flow upon intravenous administration of a test compound into dogs was tested. Compounds tested were 4-(benzothiazol-2-yl)benzylphosphonic acid ethyl isopropyl ester and, as a control, diltiazem, 4-(benzothiazol-2-yl)benzylphosphonic acid diethyl ester and 2-(benzothiazol-2-yl)-5-picolinylphosphonic acid diethyl ester.

Dogs weighing 10 to 13 kg were anaesthetized with pentobarbital sodium (35 mg/kg, intraperitoneal) and, under supportive respiration, a thoractomy was performed by removing the fourth left rib. The pericardial membrane was then incised to expose the heart. The test compound was dissolved in 50% aqueous ethanol and injected into the femoral vein. The blood flow through circumflex branch of left coronary was measured before and after the administration of drugs with an electromagnetic flowmeter (Nihon Kohden, MF-26).

Table 2 shows the results.

TABLE 2

| Compound | Dose (mg/kg) | No. of Cases | Increase in coronary blood flow (Δ% ± standard error) |
|---|---|---|---|
| 4-(Benzothiazol-2-yl)-benzylphosphonic acid ethyl isopropyl ester | 0.1 | 8 | 75.3 ± 2.9 |
| 4-(Benzothiazol-2-yl)benzylphosphonic acid diethyl ester | 0.1 | 8 | 82.2 ± 5.0 |
| 2-(Benzothiazol-2-yl)-5-picolinylphosphonic acid diethyl ester | 0.1 | 8 | 83.0 ± 12.3 |
| Diltiazem | 0.1 | 8 | 105.6 ± 14.1 |

2. Acute Toxicity

An acute toxicity test was carried out in male ddY mice (in groups of 5 animals, body weights 20±2 g) by the intraperitoneal administration of a test compound. The $LD_{50}$ values were calculated by the method of Weil based on the number of deaths within 72 hours.

The results are shown in Table 3.

TABLE 3

| Compound | $LD_{50}$ (mg/kg) |
|---|---|
| 4-(Benzothiazol-2-yl)benzylphosphonic acid ethyl isopropyl ester | 1789 |
| 4-(Benzothiazol-2-yl)benzylphosphonic acid diethyl ester | 962 |
| 2-(Benzothiazol-2-yl)-5-picolinylphosphonic acid diethyl ester | 1062 |
| Diltiazem | 177 |

The pharmaceutical compositions of this invention can be easily prepared by applying the established pharmaceutical procedure to the active compound.

Thus, an oral preparation, for instance, can be produced in the following manner. The compound, together with a pharmacologically acceptable carrier or excipient, e.g., lactose, starch, crystalline cellulose, kaolin, calcium carbonate or talc, is formed into tablets, granules, pellets or powders by the established pharmaceutical procedure. Alternatively, the compound can be suspended in an aqueous solution of carboxymethylcellulose, gum arabic or the like to make a syrup. It is also possible to prepare an injectable solution by dissolving the compound alone or together with a nonionic surfactant, such as polyoxyethylene-castor oil, in water. The compound may also be made into a suppository as formulated with a vegetable saturated fatty acid glyceride such as theobroma oil in the per se conventional manner.

While the proper relative amount of the active compound in such a preparation varies with different dosage forms, an oral dosage form, for instance, may normally contain the active compound in such an amount as will dose the subject with 1 mg to 5 mg/kg/day, whether an antianginal effect is expected or an antihypertensive effect is desired.

The following working example is given only to illustrate this invention in further detail and should by no means be construed as limiting the scope of the invention.

EXAMPLE

4-(Benzothiazol-2-yl)benzylphosphonic acid isopropyl ethyl ester 6.0 g of 4-(benzothiazol-2-yl)benzyl bromide was reacted with 4.6 g of isopropyl diethyl phosphite at 130°–140° C. for 15 minutes under nitrogen gas current while stirring. After cooling, the resulting solid precipitates were washed with n-hexane, purified by silica gel-column chromatography (eluted with benzene), and recrystallized from cyclohexane.

The title compound was obtained in a yield of 25% of theory as colorless needles melting at 96.5°–98° C.

Analysis: Calculated for $C_{19}H_{22}NO_3PS$: C:60.79; H:5.91; N:3.73, Found: C:60.75; H:6.01; N:3.84.

IR (KBr): 1240, 1050, 1010, 990, 965 cm$^{-1}$ (P=O, P—O—C)

NMR (CDCl$_3$, TMS, δppm): 1.20t-t(6 Hz, 7 Hz)9H; 3.0d(22 Hz)2H; 3.88q-d(7 Hz, 9 Hz)2H; 4.48q-d(6 Hz, 14 Hz)1H; 7.1–7.4 m 4H; 7.6–8.0 m4H.

The asymmetric type ester of the invention demonstrates high activity in increasing coronary blood flow in comparison with other asymmetric and cyclic esters of this type.

The compound possesses low acute toxicity. While the compound of the invention is somewhat lower in its activity of increasing coronary blood flow than the corresponding diethyl ester compound, it shows lower acute toxicity than such compound and thus provides a higher safety margin.

What is claimed is:

1. 4-(Benzothiazol-2-yl)benzylphosphonic acid ethyl isopropyl ester having the following formula:

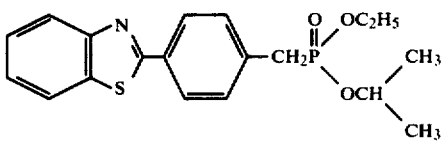

2. A coronary vasodilating composition comprising a therapeutically effective amount of 4-(benzothiazol-2-yl)benzylphosphonic acid ethyl isopropyl ester having the following formula:

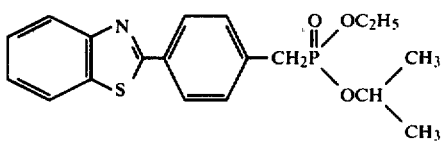

and a pharmaceutically acceptable carrier therefor.

3. A method for inducing coronary vasodilating activity in the prophylaxis or treatment of angina pectoris and hypertension, which comprises administering a safe and effective amount of 4-(benzothiazol-2-yl)benzylphosphonic acid ethyl isopropyl ester to a living animal.

* * * * *